US007589230B2

(12) United States Patent
Tiwari et al.

(10) Patent No.: US 7,589,230 B2
(45) Date of Patent: Sep. 15, 2009

(54) PROCESS FOR THE PREPARATION OF DIPHENIC ACID

(75) Inventors: Kaushal Kishore Tiwari, Jharkhand (IN); Kumares Chandra Bit, Jharkhand (IN); Sanjay Kumar Thakur, Jharkhand (IN); Kamlesh Kumar Mishra, Jharkhand (IN); Sukuru Ramakrishna Rao, Jharkhand (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/393,407

(22) Filed: Mar. 20, 2003

(65) Prior Publication Data

US 2004/0186317 A1    Sep. 23, 2004

(51) Int. Cl.
*C07C 51/255*   (2006.01)
*C07C 51/42*    (2006.01)
(52) U.S. Cl. ...................................... 562/408; 562/486
(58) Field of Classification Search ................. 562/418, 562/407, 420, 421, 408, 486; 549/232; 568/430
See application file for complete search history.

(56) References Cited

U.S. PATENT DOCUMENTS 2,786,076 A * 3/1957 O'Connor et al. ........... 562/408
3,165,547 A * 1/1965 Sauer et al. ................. 562/408

FOREIGN PATENT DOCUMENTS

EP    1 090 907    4/2001

OTHER PUBLICATIONS

The Merck Index, 8th. ed. 1968, p. 956, a copy of pp. 2.*
Lee, Ka Young, et al. *Communications* "One-Pot Conversion of Nitroarenes into N-Arylamides" Bull. Korean Chem. Soc. (2002) vol. 23, No. 10 pp. 1359-1360.
Kamal, Ahmed, et al. "An efficient reduction of azides to amines: synthesis of DNA interactive pyrrolo[2,1-c][1,4]benzodiazepines" Tetrahedron Letters (2000) vol. 41 No. 40 pp. 7743-7746.

* cited by examiner

*Primary Examiner*—Taylor Victor Oh
(74) *Attorney, Agent, or Firm*—Ladas & Parry LLP

(57) ABSTRACT

The present invention provides a process for the preparation of diphenic acid from phenanthrene which comprises heating phenanthrene and glacial acetic acid, adding drop-wise a pre-determined amount of 30% hydrogen peroxide, heating the resulting mixture after completion of drop wise addition of hydrogen peroxide, distilling the resulting mixture under reduced pressure to make the volume half, cooling the mixture till diphenic acid crystalises out, filtering the cooled mixture and boiling the residue after adding 10% solution of sodium carbonate and activated charcoal, filtering and discarding the residue; acidifying the filtrate with hydrogen chloride; cooling the resultant mixture till more diphenic acid crystallises out; repeating filtration till pure diphenic acid is obtained.

22 Claims, No Drawings

PROCESS FOR THE PREPARATION OF DIPHENIC ACID

FIELD OF THE INVENTION

The present invention relates to a process of synthesis of diphenic acid. More particularly, the present invention relates to a process of synthesis of diphenic acid from phenanthrene. The invention finds its usage in production of high temperature heat resistant resins, engineering plastics, liquid crystalline polymers, pharmaceuticals, agro-chemical industries etc. This method produces an acceptable poly-(amide-imide) resin with adequate thermal stability having good impact resistance, tensile strength or elongation properties and can be drawn as long fibres. Diphenic acid residues act as chain terminators on reaction with the aromatic diamine.

BACKGROUND OF THE INVENTION

Next to naphthalene, phenanthrene is the second largest component of high temperature coal tar. It is concentrated in anthracene oil fraction (300-360° C.) of coal tar distillation. It constitutes 30-40% of the crude anthracene cake obtained from anthracene oil by cooling and cetrifuging. After recrystalisation of anthracene residue, phenanthrene is recovered from the filtrate by solvent extraction and/or fractional distillation. Phenanthrene and its derivatives, particularly 9:10-Phenanthraquinone, 2,2'-biphenyldicarboxylic acid (Diphenic acid) and 4,4'-biphenyldicarboxylic acid are in growing demand in the world market (annual growth rate 15%) due to their excellent performance in many newly developed applications, such as production of high temperature heat resistant resins, engineering plastics, liquid crystalline polymers, pharmaceuticals and agro-chemical industries etc.

Reference is made to U.S. Pat. No. 4,352,922 wherein basic chemistry of phenanthrene-derived poly-(amide-imide) resins is described. Although this method produces an acceptable poly-(amide-imide) resin with adequate thermal stability, the resin does not have very good impact resistance, tensile strength or elongation properties and cannot be drawn as long fibres. It is thought that the deficiencies in the physical properties of the resin are due to the low molecular weight of the phenanthrene/formaldehyde reaction product and the presence therein of many oligomers of phenanthrene having terminal moieties linked to the chain at either the 9 or 10 position. On oxidation, such a reaction product will give rise to diphenic acid residues which will act as chain terminators on reaction with the aromatic diamine. R. Behrend, Zeit. Phys. Chem., 1892, 9, p. 405; 10, p. 265 describes oxidation of phenanthrene by reacting alcoholic solution of phenanthrene with chromic acid, first to phenanthre-4uinone, and then to diphenic acid but the yield and purity are poor.

Reference made to U.S. Pat. No. 4,373,089 wherein phenanthrene is converted to its 9, 10 diol derivative via 9, 10 phenanthraquinone. The phenanthrene is oxidised by a mild oxidising agent, such as potassium dichromate, to produce the phenanthraquinone which is reduced to the 9, 10 phenanthrene diol by a mild reducing agent, such as sulphur dioxide. Sulphur dioxide is a convenient reducing agent because it is possible to bubble it through a solution of the phenanthraquinone to produce the 9, 10, diol derivative. The derivative can be protected from reoxidation by a blanket of an inert gas such as nitrogen. According to a second aspect of the present invention, there is provided a polyimide resin comprising the condensation product of a reaction between an aromatic diamine and a polycarboxylated product formed by reacting the 9, 10-diol derivative of a phenanthrene with formaldehyde and oxidising the reaction product to produce keto groups bridging the diphenic acid moieties produced. According to a third aspect of the present invention, there are provided intermediates in the formation of a polyimide resin comprising firstly the reaction product of a 9, 10-diol derivative of a phenanthrene with formaldehyde in the presence of an acid catalyst, and secondly the reaction product which has been oxidised to produce keto groups bridging the diphenic acid moieties produced.

Prior art search for production of diphenic acid was done based on literature survey and patent databases and did not yield any relevant references.

OBJECTS OF THE INVENTION

The main object of the invention is to provide a process of synthesis of diphenic acid from phenanthrene which obviates the drawbacks as detailed above.

Another object of the invention is to obtain 99% pure diphenic acid.

Yet another object of the invention is to provide a process for the preparation of diphenic acid which is simple and eco-friendly.

It is another object of the invention to provide a process for the synthesis of diphenic acid which is economical.

SUMMARY OF THE INVENTION

Accordingly the present invention provides a process for the preparation of diphenic acid from phenanthrene which comprises (i) heating phenanthrene and glacial acetic acid,
(ii) adding drop-wise a pre-determined amount of 30% hydrogen peroxide,
(iii) heating the resulting mixture after completion of drop wise addition of hydrogen peroxide,
(iv) distilling the resulting mixture under reduced pressure to make the volume half,
(v) cooling the mixture till diphenic acid crystalises out,
(vi) filtering the cooled mixture and boiling the residue after adding 10% solution of sodium carbonate and activated charcoal,
(vii) filtering and discarding the residue;
(viii) acidifying the filtrate with hydrogen chloride;
(ix) cooling the resultant mixture till more diphenic acid crystallises out;
(x) repeating filtration till pure diphenic acid is obtained.

In one embodiment of the invention, the heating in step (i) above is done in a reactor at a temperature in the range of 75 to 85° C.

In another embodiment of the invention, 30% hydrogen peroxide is added drop wise in an amount in the range of 100 to 300 ml, for a time period in the range of 30 to 60 minutes.

In yet another embodiment of the invention, the heating in step (iii) is done for a time period in the range of 3 to 7 hours.

In yet another embodiment of the invention, the residue in step (vi) is boiled at 100° C. after adding 10% solution of sodium carbonate and activated charcoal for decolouration.

In a further embodiment of the invention, the acid is added to maintain the pH of the mixture in the range of 3 to 4.5.

In another embodiment of the invention, the amounts of phenanthrene and glacial acetic acid added are in the ratio of 1:10 to 1:12 (w/w).

In a further embodiment of the invention, the purity of diphenic acid produced is 99%.

DETAILED DESCRIPTION OF THE INVENTION

Phenanthrene and glacial acetic acid are added together in a reactor and heated up within 75-85° C. To the resulting mixture, 100-300 ml of 30% hydrogen peroxide solution is added drop wise, which takes between 30-60 minutes. After completion of addition of hydrogen peroxide solution, the temperature of 75-85° C. is further maintained for a time period ranging between 3 to 4 hours. The resulting mixture is subjected to distillation, under reduced pressure, to make the volume half and the mass is allowed to cool. On cooling, considerable amount of diphenic acid crystallises out.

The cooled mixture is filtered and the residue is boiled at 100° C. after addition of 10% solution of sodium carbonate and activated charcoal (for decolouration) and subjected to filtration after which the residue is discarded and the filtrate is acidified with hydrogen chloride to maintain the pH at 4.5 and cooled where diphenic acid crystallises out. This process is repeated several times till pure diphenic acid is obtained having melting point at 228-229° C.

The phenanthrene and glacial acetic acid added are preferably in a ratio of 1:10 (w/w). It is observed that the purity of diphenic acid produced is about 99%.

The novelty of the present invention resides in slow and controlled oxidation of phenanthrene (drop wise addition of the oxidising agent at a specific temperature range and a specific time range, which was unknown in the prior art). This method produces an acceptable poly-(amide-imide) resin with adequate thermal stability having good impact resistance, tensile strength or elongation properties and which can be drawn as long fibres. Diphenic acid residues act as chain terminators on reaction with the aromatic diamine. The method of the invention can be used in many newly developed field of applications e.g. production of heat resistant resins, engineering plastics, liquid crystalline polymers, pharmaceuticals, agro-chemical industries etc. from phenanthrene, which was otherwise unutilised due to cost factors. The present process was proved to enhance the yield of diphenic acid drastically.

The following examples are given by way of illustration and should not be construed to limit the scope of the present invention.

EXAMPLE-1

25 grams of Phenanthrene and 253 grams glacial acetic acid are added together in a reactor and heated up to 85° C. To the resulting mixture, 100 ml of 30% hydrogen peroxide solution is added drop wise, which normally takes 40 minutes. After completion of addition of hydrogen peroxide solution, the temperature of 85° C. is further maintained for a time period of 6 hours. The resulting mixture is subjected to distillation, under reduced pressure, to make the volume half and the mass is allowed to cool. On cooling, considerable amount of diphenic acid crystallises out. The cooled mixture is filtered and the residue is boiled at 100° C. after addition of 10% solution of sodium carbonate and activated charcoal (for decolouration) and subjected to filtration after which the residue is discarded and the filtrate is acidified with hydrogen chloride to maintain the pH at 4.5 and cooled where diphenic acid crystallises out. This process is repeated several times till pure diphenic acid is obtained having melting point at 228° C. Yield obtained was 11 grams.

EXAMPLE-2

25 grams Phenanthrene and 253 grams glacial acetic acid are added together in a reactor and heated up to 85° C. To the resulting mixture, 200 ml of 30% hydrogen peroxide solution is added drop wise, which normally takes 40 minutes. After completion of addition of hydrogen peroxide solution, the temperature of 85° C. is further maintained for a time period 6 hours. The resulting mixture is subjected to distillation, under reduced pressure, to make the volume half and the mass is allowed to cool. On cooling, considerable amount of diphenic acid crystalises out. The cooled mixture is filtered and the residue is boiled at 100° C. after addition of 10% solution of sodium carbonate and activated charcoal (for decolouration) and subjected to filtration after which the residue is discarded and the filtrate is acidified with hydrogen chloride to maintain the pH at 4.5 and cooled where diphenic acid crystallises out. This process is repeated several times till pure diphenic acid is obtained having melting point at 229° C. The yield obtained was 17 grams.

EXAMPLE-3

25 grams Phenanthrene and 253 grams of glacial acetic acid are added together in a reactor and heated up to 85° C. To the resulting mixture, 88 ml of 30% hydrogen peroxide solution is added drop wise, which normally takes 30 minutes. After completion of addition of hydrogen peroxide solution, the temperature of 80° C. is further maintained for a time period of 3.5 hours. The resulting mixture is subjected to distillation, under reduced pressure, to make the volume half and the mass is allowed to cool. On cooling, considerable amount of diphenic acid crystalises out. The cooled mixture is filtered and the residue is boiled at 100° C. after addition of 10% solution of sodium carbonate and activated charcoal (for decolouration) and subjected to filtration after which the residue is discarded and the filtrate is acidified with hydrogen chloride to maintain the pH at 4.5 and cooled where diphenic acid crystallises out. This process is repeated several times till pure diphenic acid is obtained having melting point at 229° C. The yield is 12 gms.

The Main Advantages of the Present Invention are:
1. The process is very simple and eco-friendly.
2. The yield of the product is very high in comparison to prior art.
3. No side reactions are involved in the process.

We claim:
1. A process for the preparation of diphenic acid from phenanthrene which comprises the steps of
   (i) heating phenanthrene and glacial acetic acid at a temperature in a range of 75 to 85° C. to form a mixture consisting essentially of the phenanthrene and the glacial acetic acid,
   (ii) adding drop-wise a pre-determined amount of a 30% solution hydrogen peroxide over a period of from 30 to 60 minutes to form a resulting mixture consisting essentially of the phenanthrene, the glacial acetic acid, the hydrogen peroxide and water,
   (iii) heating the resulting mixture for 3 to 7 hours after completion of drop-wise addition of hydrogen peroxide solution,
   (iv) distilling the resulting mixture under reduced pressure to make the volume half,
   (v) cooling the mixture until diphenic acid crystalises out,

(vi) filtering the cooled mixture to form a residue and a filtrate, and boiling the residue after adding 10% solution of sodium carbonate and activated charcoal, (vii) filtering and discarding the residue;

(viii) acidifying the filtrate with hydrogen chloride to form a resultant mixture;

(ix) cooling the resultant mixture until more diphenic acid crystallises out; and (x) repeating filtration till pure diphenic acid is obtained.

2. A process as claimed in claim 1 wherein the 30% hydrogen peroxide solution is added drop-wise in an amount in the range of 100 to 300 ml.

3. A process as claimed in claim 1 wherein the residue in step (vi) is boiled at 100° C. after adding 10% solution of sodium carbonate and activated charcoal for decolouration.

4. A process as claimed in claim 1 wherein the acidifying in step (viii) comprises adding the hydrogen chloride in an amount sufficient to maintain pH of the mixture in the range of 3 to 4.5.

5. A process as claimed in claim 1 wherein the amounts of phenanthrene and glacial acetic acid are in ratio of 1:10 to 1:12 (w/w).

6. A process as claimed in claim 1 wherein the purity of diphenic acid produced is 99%.

7. A process for the preparation of diphenic acid from phenanthrene which comprises the steps of heating phenanthrene and glacial acetic acid in a reactor at a temperature in the range of 75 to 85° C., adding 30% hydrogen peroxide solution drop-wise, the amount of hydrogen peroxide being in the range of 100 to 300 ml, for a time period in the range of 30 to 60 minutes to form a resulting mixture consisting essentially of the phenanthrene, the glacial acetic acid, the hydrogen peroxide and water, heating the resulting mixture after completion of drop-wise addition of hydrogen peroxide solution for a time period in the range of 3 to 7 hours, subjecting the resulting mixture to distillation under reduced pressure to make the volume half, cooling the mixture until a considerable amount of diphenic acid crystallises out, filtering the cooled mixture to form a filtrate and a residue; boiling the residue at 100° C. after addition of 10% solution of sodium carbonate and activated charcoal for decolouration and discarding the residue acidifying the filtrate with hydrogen chloride to maintain a pH of 4.5; cooling the resultant mixture until diphenic acid crystallises out; and repeating filtration several times until pure diphenic acid is obtained having a melting point at 228-229° C.

8. In a process for the preparation of diphenic acid from phenanthrene, comprising the steps of (i) combining phenanthrene with glacial acetic acid and heating to form a mixture, (ii) oxidizing the phenanthrene by adding an oxidizing agent consisting of a solution of hydrogen peroxide to the mixture and heating, (iii) distilling the mixture under reduced pressure to reduce the volume of the mixture, (iv) cooling and filtering the reduced-volume mixture to obtain a filtrate comprising diphenic acid, and (vi) recovering diphenic acid by neutralization, filtration and acidification, the improvement wherein the mixture to which the solution of hydrogen peroxide is added in step (ii) consists essentially of the phenanthrene and the glacial acetic acid whereby a resulting mixture is formed consisting essentially of the phenanthrene, the glacial acetic acid, the hydrogen peroxide and water, and wherein the process further comprises controlling the oxidizing of the phenanthrene in step (ii) to enhance the yield of diphenic acid by drop-wise addition of the hydrogen peroxide solution to the mixture over a period of from 30 to 60 minutes while the mixture is maintained at a temperature in the range of 75 to 85° C.

9. The process as claimed in claim 8, wherein after completion of the drop-wise addition of the hydrogen peroxide solution in step (ii), the mixture is maintained at the temperature of 75-85° C. for a time period in the range of 3 to 7 hours.

10. The process as claimed in claim 9, wherein the solution of hydrogen peroxide is a 30% solution that is added dropwise in step (ii) in an amount of 100 to 300 ml.

11. The process as claimed in claim 10, wherein the phenanthrene and glacial acetic acid are combined in step (i) in a ratio of 1:10 to 1:12 (w/w).

12. The process as claimed in claim 11, wherein the acidifying in step (v) comprises adding hydrogen chloride to the filtrate in an amount sufficient to maintain a pH of 3 to 4.5.

13. The process as claimed in claim 12, wherein the process comprises further filtration steps to obtain pure diphenic acid with a melting point at 228-229° C.

14. The process as claimed in claim 1, wherein the resulting mixture consists of the phenanthrene, the glacial acetic acid, the hydrogen peroxide and water.

15. The process as claimed in claim 7, wherein the resulting mixture consists of the phenanthrene, the glacial acetic acid, the hydrogen peroxide and water.

16. The process as claimed in claim 8, wherein the resulting mixture consists of the phenanthrene, the glacial acetic acid, the hydrogen peroxide and water.

17. The process as claimed in claim 1, which consists essentially of said steps.

18. The process as claimed in claim 7, which consists essentially of said steps.

19. The process as claimed in claim 1, which consists of said steps.

20. The process as claimed in claim 7, which consists of said steps.

21. The process as claimed in claim 1, wherein the phenanthrene and glacial acetic acid are combined in step (i) in a ratio of 1:10 (w/w).

22. The process as claimed in claim 1, wherein the 30% solution of hydrogen peroxide is added dropwise in step (ii) in an amount of 100 ml to 25 grams of phenanthrene.

* * * * *